(12) United States Patent
O'Lenick

(10) Patent No.: US 8,471,047 B1
(45) Date of Patent: Jun. 25, 2013

(54) MIXED GLYCERYL ESTERS

(75) Inventor: Kevin A. O'Lenick, Dacula, GA (US)

(73) Assignee: Surfatech Corporation, Lawrenceville, GA (US)

( * ) Notice: Subject to any disclaimer, the term of this patent is extended or adjusted under 35 U.S.C. 154(b) by 331 days.

(21) Appl. No.: 12/930,500

(22) Filed: Jan. 10, 2011

Related U.S. Application Data

(60) Provisional application No. 61/459,189, filed on Dec. 9, 2010.

(51) Int. Cl.
*A23D 9/00* (2006.01)

(52) U.S. Cl.
USPC ........... 554/227; 554/224; 554/163; 554/166; 554/172

(58) Field of Classification Search
None
See application file for complete search history.

(56) References Cited

U.S. PATENT DOCUMENTS

| | | | |
|---|---|---|---|
| 4,918,063 A * | 4/1990 | Lichtenberger | 514/78 |
| 6,677,470 B2 * | 1/2004 | Saebo et al. | 554/227 |
| 7,550,623 B2 | 6/2009 | Ehara | |

OTHER PUBLICATIONS

Svensson, L., et al., The relationship between the structure of monoalkyl branched saturated triacylglycerols and some physical properties, 1997, Lipids, vol. 32, No. 6, pp. 661-666.*
Vajdi, M., et al., Identificatin of adduct radiolysis products from pork fat, 1985, JAOCS, vol. 62, No. 8, pp. 1252-1260.*

* cited by examiner

*Primary Examiner* — Yate K Cutliff

(57) ABSTRACT

The present invention relates to a series of mixed esters of glycerin esters having two distinct alkyl groups present thereon. One is a low melting product, having a melting point of below 70° C. and the other having a melting point of above 90° C. The presence of the two different melting point groups on the glycerin results in a modification of the hardness, spredability and aesthetics of the resulting mixed ester. This ability to alter hardness and skin aesthetics makes the products of the present invention useful in personal care products ranging as additives to pigmented products to minimize syneresis, to stick products alter the hardness, shrinkability and aesthetics of the stick, to pressed powders where they act to modify the compressability of the powders to which they are added as well as the feel achieved when they are applied to the skin.

11 Claims, No Drawings

MIXED GLYCERYL ESTERS

RELATED APPLICATION

This application claims priority to and benefit of U.S. Provisional Application Nos. 61/459,189, filed Dec. 9, 2010, the disclosures of each of which are incorporated herein for all purposes.

FIELD OF THE INVENTION

The present invention relates to a series of mixed esters of glycerin esters having two distinct alkyl groups present thereon. One is derived from a low melting fatty acid, having a melting point of below 70° C. and the other is derived from a high melting fatty acid having a melting point of above 90° C. The presence of the two different melting point groups on the glycerin results in a modification of the hardness, spreadability and aesthetics of the resulting mixed ester. This ability to alter hardness and skin aesthetics makes the products of the present invention useful in personal care products ranging as additives to pigmented products to minimize syneresis, to stick products alter the hardness, shrinkability and aesthetics of the stick, to pressed powders where they act to modify the compressability of the powders to which they are added as well as the feel achieved when they are applied to the skin.

BACKGROUND OF THE INVENTION

Glyceryl esters are a widely known class of compounds. They are naturally occurring materials in both the plant and animal world. The natural occurring Glyceryl esters are referred to as triglycerides and are the result of very specific enzymes used by living systems to get highly specialized molecules. These include olive oil, soybean oil and coconut oil. These esters don not contain any fatty groups above C22. An essential element of the present invention is high molecular weight high melting point fatty acids derived from ethylene, which is subsequently oxidized using nickel catalyst. It is this high molecular weight fatty acid in a random molecule with lower melt point fatty acids that allows for control of the properties like hardness, spread on the skin and aesthetics.

The variation in alkyl chain length in naturally occurring products is quite small. Since the triglycerides made in nature are designed as an energy source for the plant or animal, the carbon chain variation is quite small, generally at 18 carbon atoms.

Triglycerides are natural products that are provided to plants and animals as a storage molecule for energy to be used by the plant or animal when needed.

Typical glyceryl esters are disclosed in U.S. Pat. No. 7,550,623, incorporated herein by reference. The invention teaches "The present invention provides a liquid ester composition which is obtained by esterifying a branched isostearic acid such as 2-(1,3,3-trimethyl)butyl-5,7,7-trimethyl octanoic acid with dipentaerythritol, and said liquid ester composition having a viscosity at 25.degree. C. of 100,000 to 2,000,000 mPas; hydroxyl value of 10 to 160; and cloud point of less than 5° C."

Fats occur naturally in food and play a significant role in human nutrition. Fats are used to store energy in the body, insulate body tissues, cushion internal organs, and transport fat-soluble vitamins in the blood.

Fats are the most prevalent class of compounds (in living systems) referred to as lipids. Lipids are cellular compounds that are insoluble in water. Fats are soft, low-melting solids, with a density less than that of water. They have a greasy feel and are slippery. Fats and closely related oils are mixtures of compounds consisting of fatty acids combined with glycerol (commonly known as glycerin) via ester linkages. Fatty acids are long, straight chain carboxylic acids. A fat (or oil) is formed when three fatty acid molecules react with a glycerol molecule to yield a triglyceride (and three water molecules). Fats in the body are transported and stored as triglycerides.

The compounds of the present invention are glyceryl esters that contain both high melting groups (not naturally occurring) and lower melting point groups in the same molecule. The placement of these groups in the same molecule as will become clear from reading the specification of this invention, results in a unique ability to alter a combination of properties, including hardness, rheology and skin aesthetics. It is very important to note that each of the hydroxyl groups on the glycerin are randomly either have a high melting or low melting group thereon. This is a direct consequence of the fact that from a reactivity point of view each hydroxyl group is as reactive as each other on glycerin (no regiospecificity) and each carboxyl on each acid is equally reactive, resulting in a totally random glyceryl ester. This is the exact opposite of what happens in nature, where each group is carefully controlled using enzyme systems possessed by the living plant or animal making such esters biologically. This random pattern is critical to the functionality making the resulting mixed ester very unlikely to form highly organized crystalline waxes, rather forming amphorous solids and butter like products.

We have determined that the difference in melting point of at least 20° C. is a critical factor in the present invention. When the range of melt point is this far apart (i.e. the difference between the high melting point acid and the low melting point acid,) the resulting product has a softness that confers a butter like consistency. Without wanting to be held to one particular explanation, we believe that when the difference is that great a fractional solidification occurs upon cooling resulting in an appreciable amount of time where there are both solid and liquid domains in the cooling wax. This lack of uniformity results in the "disrupted wax" being formed. In a preferred embodiment, the lower melting acid is liquid at ambient temperature and never becomes solid under ambient temperatures, which is the temperature of application for personal care products.

THE INVENTION

Objective of the Invention

It is the object of the present invention to provide a series of glyceryl esters that are made by the esterification of glycerin with a mixture of carboxylic acids having a melt point above 90° C. and fatty acids having a melt point below 70° C.

It is additionally an object of the invention to provide a process for using the esters of the present invention in a process for conditioning hair and skin which comprises contacting the hair or skin with a glyceryl ester that was made by the esterification of glycerin with a mixture of carboxylic acids having a melt point above 90° C. and fatty acids having a melt point below 70° C.

All temperatures are given in degrees C, all percentages in percent by weight, unless otherwise specified. All patents referenced herein are incorporated by reference as allowed.

SUMMARY OF THE INVENTION

The present invention is drawn to a series of glyceryl esters that are made by the esterification of glycerin with a mixture of carboxylic acids having a melt point above 90° C. and fatty acids having a melt point below 70° C.

Additionally, the invention is drawn to a process for using the esters of the present invention in a process for conditioning hair and skin which comprises contacting the hair or skin with a glyceryl ester that was made by the esterification of glycerin with a mixture of carboxylic acids having a melt point above 90° C. and fatty acids having a melt point below 70° C.

DETAILED DESCRIPTION OF THE INVENTION

One aspect of the present invention is a mixed glyceryl ester made by the esterification reaction of
(a) glycerin which conforms to the following structure:

and
(b) a mixture of
1) a fatty acid having a melting point of below 70° C. conforming to the following structure:

wherein
R' is alkyl or alkylene having 6 to 18 carbon atoms;
2) a fatty acid having a melting point of above 90° C. conforming to the following structure:

wherein
$R^2$ is alkyl having 30 to 60 carbon atoms.

The two types of fatty acids are mixed together with the glycerin and heated to between 150 and 200° C., preferably between 160 and 180° C. for 4 to 10 hours while water is distilled off. Since there is no specificity of reaction of the three hydroxyl groups with either of the fatty acids reacted a truly mixed ester results.

The present invention is drawn to a series of glyceryl esters that conform to the following structure;

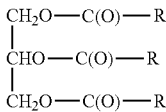

wherein
R is a mixture of
(a) a lower carbon alkyl or alkylene having 5 to 17 carbon atoms;
and
(b) a higher carbon alkyl having between 29 and 59 carbon atoms.

The presence of two different melt point carboxylic acids in the same molecule, allows one to make a high melting point solid that has domains of lowering melting groups that inhibit formation of crystalline hard waxes. The disruption caused by the different melting point groups prevents the material from solidifying uniformly and gives products with unique rehology and feel properties on the skin.

The products with less than 50% of the total carboxylic groups added that have a high melting point are softer, more thyrotrophic and spread better on the skin. A preferred concentration of 1 to 2 parts of the high melting carboxylic acid the low melting products provide great skin feel. A more preferred concentration of 1 to 5 parts of the high melting carboxylic acid the low melting products provide products that liquefy under pressure.

The products with more than 50% of the total carboxylic groups added that have a high melting point are harder, more waterproof on the skin and provide stick hardness to lipsticks and antiperspirant compositions.

Preferred Embodiment

In a preferred embodiment the ratio of high melting group fatty acid with a higher carbon alkyl having between 49 and 59 carbon atoms to low melting group fatty acid with a lower carbon alkyl or alkylene having 5 to 17 carbon atoms is 1:1 by weight.

In a preferred embodiment the ratio of high melting group fatty acid with a higher carbon alkyl having between 49 and 59 carbon atoms to low melting group fatty acid with a lower carbon alkyl or alkylene having 5 to 17 carbon atoms is 2:1 by weight.

In a preferred embodiment the ratio of high melting group fatty acid with a higher carbon alkyl having between 49 and 59 carbon atoms to low melting group fatty acid with a lower carbon alkyl or alkylene having 5 to 17 carbon atoms is 1:2 by weight.

In a preferred embodiment the ratio of high melting group fatty acid with a higher carbon alkyl having between 49 and 59 carbon atoms to low melting group fatty acid with a lower carbon alkyl or alkylene having 5 to 17 carbon atoms is 1:5 by weight.

In a preferred embodiment the ratio of high melting group fatty acid with a higher carbon alkyl having between 49 and 59 carbon atoms to low melting group fatty acid with a lower carbon alkyl or alkylene having 5 to 17 carbon atoms is 5:1 by weight.

In a preferred embodiment the ratio of high melting group fatty acid with a higher carbon alkyl having between 49 and 59 carbon atoms to low melting group fatty acid with a lower carbon alkyl or alkylene having 5 to 17 carbon atoms is 10:1 by weight.

In a preferred embodiment the ratio of high melting group fatty acid with a higher carbon alkyl having between 49 and 59 carbon atoms to low melting group fatty acid with a lower carbon alkyl or alkylene having 5 to 17 carbon atoms is 1:10 by weight.

EXAMPLES

Glycerin is an item of commerce and conforms to the following structure:

The CAS number is 56-81-5
The EINECS number is 200-289-5.

Fatty Acids

Fatty acids, also known as carboxylic acids are common items of commerce.

| Melt point above 90° C. | | | | |
|---|---|---|---|---|
| Example | Carbon Atoms | Acid Value | Commercial Name | Melt Point (° C.) |
| 1 | C29 | 120 | Unicid ® 350 | 92 |
| 2 | C49 | 79 | Unicid ® 550 | 101 |
| 3 | C59 | 63 | Unicid ® 750 | 110 |

Unicid® is a registered trademark of Baker Petrolite. The molecular weight for reaction purposes was calculated as from the acid value. The trade name is given merely for reference.

| B Melt point below 70° C. | | | |
|---|---|---|---|
| Example | Carbon Atoms | Name | Melt Point (° C.) |
| 4 | C7 | Capric Acid | −3 |
| 5 | C9 | Caprylic Acid | 16 |
| 6 | C11 | Lauric Acid | 44 |
| 7 | C13 | Myristic Acid | 55 |
| 8 | C15 | Palmitic Acid | 63 |
| 9 | C17 | iso-stearic Acid | −30 |
| 10 | C17(one unsaturation) | Oleic Acid | 16 |
| 11 | C17 (two unsaturation) | Linoleic Acid | −5 |

General Procedure

The esters of the current invention are made as follows
To a glass flask having a thermometer, stirring and vacuum is added 92.0 grams of glycerin. Next add the carboxylic acid having a melt point above 85° C. (examples 1-3), next add the fatty acids (example 4-11). Finally, add 0.1 percent by weight of stannous oxylate (based upon the total weight of other ingredients added. Heat to 180° C. Water will begin to distill off as the temperature reaches around 150 C. Hold the temperature at 180-190 C until the acid value is less than 5 mg KOH/gm.

| | Carboxylic Acid (Example 1-3) | | Fatty Acid (Example 4-11) | |
|---|---|---|---|---|
| Example | Example | Grams | Example | Grams |
| 12 | 1 | 700 | 4 | 216 |
| 13 | 2 | 1065 | 5 | 300 |
| 14 | 3 | 1335 | 6 | 342 |
| 15 | 1 | 700 | 7 | 382 |
| 16 | 2 | 1065 | 8 | 426 |
| 17 | 3 | 1335 | 9 | 426 |
| 18 | 1 | 700 | 10 | 423 |
| 19 | 2 | 1065 | 11 | 420 |
| 20 | 3 | 890 | 4 | 288 |
| 21 | 1 | 467 | 5 | 344 |
| 22 | 2 | 710 | 6 | 400 |
| 23 | 3 | 890 | 7 | 456 |
| 24 | 1 | 467 | 8 | 512 |
| 25 | 2 | 710 | 9 | 568 |
| 26 | 3 | 890 | 10 | 564 |
| 27 | 1 | 172 | 11 | 560 |
| 28 | 1 | 934 | 4 | 144 |
| 29 | 2 | 1420 | 5 | 172 |
| 30 | 3 | 1780 | 6 | 200 |
| 31 | 1 | 934 | 7 | 228 |
| 32 | 2 | 1420 | 8 | 256 |
| 33 | 3 | 1780 | 9 | 284 |
| 34 | 1 | 934 | 10 | 282 |
| 35 | 2 | 1420 | 11 | 280 |

This ability to alter hardness and skin aesthetics makes the products of the present invention useful in personal care products ranging as additives to pigmented products to minimize syneresis, to stick products alter the hardness, shrinkability and aesthetics of the stick, to pressed powders where they act to modify the compressability of the powders to which they are added as well as the feel achieved when they are applied to the skin While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A mixed glyceryl ester that conforming to the following structure;

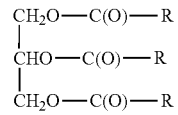

wherein;
R is a mixture of
(a) a lower carbon alkyl or alkylene having 5 to 17 carbon atoms;
and
(b) a higher carbon alkyl having between 49 and 59 carbon atoms.

2. A mixed glyceryl ester of claim 1 wherein said higher carbon alkyl has 49 carbon atoms.

3. A mixed glyceryl ester of claim 1 wherein said higher carbon alkyl has 59 carbon atoms.

4. A mixed glyceryl ester of claim 1 wherein said lower carbon alkyl has 17 carbon atoms.

5. A mixed glyceryl ester of claim 1 wherein the ratio higher carbon alkyl to lower carbon alky or alkylene is 1:1 by weight.

6. A mixed glyceryl ester of claim 1 wherein the ratio higher carbon alkyl to lower carbon alky or alkylene is 2:1 by weight.

7. A mixed glyceryl ester of claim 1 wherein the ratio higher carbon alkyl to lower carbon alkyl or alkylene is 1:2 by weight.

8. A mixed glyceryl ester of claim 1 wherein the ratio higher carbon alkyl to lower carbon alkyl or alkylene is 1:5 by weight.

9. A mixed glyceryl ester of claim 1 wherein the ratio higher carbon alkyl to lower carbon alkyl or alkylene is 5:1 by weight.

10. A mixed glyceryl ester of claim 1 wherein the ratio higher carbon alkyl to lower carbon alkyl or alkylene is 10:1 by weight.

11. A mixed glyceryl ester of claim 1 wherein the ratio higher carbon alkyl to lower carbon alkyl or alkylene is 1:10 by weight.

* * * * *